(12) United States Patent
Kikuchi

(10) Patent No.: US 8,951,044 B2
(45) Date of Patent: Feb. 10, 2015

(54) KEEPER FOR IMPLANT AND ITS ASSEMBLY, AND KEEPER-FIXING METHOD

(75) Inventor: Akira Kikuchi, Takasaki (JP)

(73) Assignee: Hitachi Metals, Ltd., Tokyo (JP)

( * ) Notice: Subject to any disclaimer, the term of this patent is extended or adjusted under 35 U.S.C. 154(b) by 0 days.

(21) Appl. No.: 14/119,691

(22) PCT Filed: May 22, 2012

(86) PCT No.: PCT/JP2012/063022
§ 371 (c)(1),
(2), (4) Date: Nov. 22, 2013

(87) PCT Pub. No.: WO2012/161182
PCT Pub. Date: Nov. 29, 2012

(65) Prior Publication Data
US 2014/0141387 A1    May 22, 2014

(30) Foreign Application Priority Data

May 25, 2011    (JP) .................................. 2011-117383

(51) Int. Cl.
*A61C 8/00*    (2006.01)
*A61C 19/02*   (2006.01)
*A61C 13/235*  (2006.01)

(52) U.S. Cl.
CPC .............. *A61C 19/02* (2013.01); *A61C 13/235* (2013.01); *A61C 8/005* (2013.01); *A61C 8/0081* (2013.01); *A61C 8/0068* (2013.01); *A61C 8/0059* (2013.01); *A61C 8/0069* (2013.01); *A61C 8/0074* (2013.01)
USPC .......................................................... 433/189

(58) Field of Classification Search
CPC ............................ A61C 8/0068; A61C 8/0081
USPC ................................................. 433/173, 189
See application file for complete search history.

(56) References Cited

U.S. PATENT DOCUMENTS

| 4,722,688 A | 2/1988 | Lonca |
| 5,145,371 A | 9/1992 | Jorneus |

(Continued)

FOREIGN PATENT DOCUMENTS

| JP | 58-112536 A | 7/1983 |
| JP | 62-284642 A | 12/1987 |

(Continued)

OTHER PUBLICATIONS

International Search Report of PCT/JP2012/063022 dated Aug. 28, 2012).

*Primary Examiner* — Ralph Lewis
(74) *Attorney, Agent, or Firm* — Sughrue Mion, PLLC

(57) ABSTRACT

A keeper for an implant comprising (a) a keeper body made of a soft-magnetic material, which comprises a recess for receiving a head of an abutment having a female thread, and a female thread extending along a center axis to have communication with the recess and having a larger nominal diameter than that of the female thread of the abutment; and (b) a stepped screw member comprising a small-diameter screw portion threadably engageable with the female thread of the abutment, and a large-diameter screw portion threadably engageable with the female thread of the keeper body; the keeper body being strongly fixed to the abutment by the stepped screw member, when the keeper body is rotated in a threadably engaging direction, after the female thread of the abutment threadably engages the small-diameter screw portion, and after the female thread of the keeper body threadably engages the large-diameter screw portion.

16 Claims, 13 Drawing Sheets

(56) References Cited

U.S. PATENT DOCUMENTS

| | | |
|---|---|---|
| 5,358,367 A | 10/1994 | Yang |
| 5,658,147 A | 8/1997 | Phimmasone |
| 6,325,803 B1 * | 12/2001 | Schumacher et al. .......... 606/71 |
| 6,709,270 B2 | 3/2004 | Honkura et al. |
| 7,905,727 B2 | 3/2011 | Kikuchi |
| 2002/0123022 A1 * | 9/2002 | Pilla et al. .................... 433/173 |
| 2003/0124491 A1 | 7/2003 | Honkura et al. |
| 2007/0105068 A1 * | 5/2007 | Stucki-McCormick ...... 433/173 |
| 2008/0299515 A1 * | 12/2008 | Duncan ........................ 433/174 |
| 2009/0117520 A1 | 5/2009 | Kikuchi |
| 2013/0209958 A1 * | 8/2013 | Benz et al. .................... 433/173 |

FOREIGN PATENT DOCUMENTS

| | | |
|---|---|---|
| JP | 03-121065 A | 5/1991 |
| JP | 10-314186 A | 12/1998 |
| JP | 2008-93126 A | 4/2008 |
| JP | 2009-131620 A | 6/2009 |
| WO | 2005/077297 A1 | 8/2005 |

* cited by examiner

KEEPER FOR IMPLANT AND ITS ASSEMBLY, AND KEEPER-FIXING METHOD

CROSS REFERENCE TO RELATED APPLICATIONS

This is a National Stage of International Application No. PCT/JP2012/063022 filed May 22, 2012 (claiming priority based on Japanese Patent Application No. 2011-117383 filed May 25, 2011), the contents of which are incorporated herein by reference in their entirety.

FIELD OF THE INVENTION

The present invention relates to a keeper for an implant for fixing a magnetic attachment for a denture to an implant body, its assembly, and a keeper-fixing method.

BACKGROUND OF THE INVENTION

In a dental implant treatment, an easily detachable denture-fixing method comprising fixing a keeper made of a soft-magnetic material to an implant body implanted in the jawbone and magnetically attaching a magnet-containing denture attachment to the keeper is recently used widely.

U.S. Pat. No. 6,709,270 discloses, as shown in FIG. 15, a magnetic dental attachment comprising a keeper 103 made of a soft-magnetic material and threadably engaging an implant body 110, and a denture attachment 105 containing a magnet 155, which is magnetically attached to the keeper 103. The keeper 103 comprises a conically tapered upper portion 135, and a ring portion 137 projecting from an upper peripheral surface of the conically tapered portion 135 and having a circular groove on the rear side. The implant body 110 comprises a conically tapered recess 115 complementary to the tapered portion 135 of the keeper 103. When the keeper 103 threadably engages the implant body 110, a tip end portion of the ring portion 137 of the keeper 103 abuts an upper end portion of the implant body 110, so that tip end portion of the ring portion 137 is elastically deformed radially. Tension generated by this elastic deformation prevents the keeper 103 from loosening. However, because the tip end portion of the ring portion 137 is in contact with the upper end portion of the implant body 110 in a small area in the denture attachment of U.S. Pat. No. 6,709,270, the plastic deformation of the ring portion 137 after a long period of use is likely to decrease the tension, resulting in the loosening of the keeper 110.

JP 2009-131620 A discloses, as shown in FIG. 16, a keeper assembly for an implant comprising (a) an implant body 205; (b) an abutment 204 comprising a head 241 having a female thread 243 and threadably engageable with the implant body 205; (c) a keeper body 202 made of a soft-magnetic material, which comprises a recess 221 for receiving the head 241 of the abutment 204, and a female thread 222 extending along a center axis to have communication with the recess 221; and (d) a screw member 203 threadably engageable with the female thread 222 of the keeper body 202 and the female thread 243 of the abutment 204; the screw member 203 being threadably engaged with the female thread 222 of the keeper body 202 and the female thread 243 of the abutment 204 after the keeper body 202 threadably engages the abutment 204 threadably engaging the implant body 205. However, because the screw member 203 does not have a portion abutting the keeper body 202 or the abutment 204, the axial position of the screw member 203 threadably engaging the keeper body 202 and the abutment 204 should be adjusted manually.

In addition, because the head of the keeper body 202 is as extremely thin as about 1 mm, the female thread 222 of the keeper body 202 has screw ridges only in the minimum number (about 3 or 4) necessary for threadable engagement with the screw member 203. Accordingly, if the threadably engaging position of the screw member 203 were shifted toward the abutment 204, a sufficient fastening strength would not be obtained between the keeper body 202 and the screw member 203. Also, if shifted in an opposite direction, the head of the screw member 203 wound project from the upper surface of the keeper body 202, necessitating the precise manual positioning of the screw member 203.

OBJECTS OF THE INVENTION

Accordingly, an object of the present invention is to provide a keeper for an implant threadably engageable with an abutment precisely and easily, without loosening even after a long period of use.

Another object of the present invention is to provide a method for fixing the above keeper for an implant to an abutment.

A further object of the present invention is to provide a keeper assembly for an implant comprising a keeper body, an abutment, and a screw member for threadably engaging them.

DISCLOSURE OF THE INVENTION

The keeper for an implant of the present invention comprises (a) a keeper body made of a soft-magnetic material, which comprises a recess for receiving a head of an abutment having a female thread, and a female thread extending along a center axis to have communication with the recess and having a larger nominal diameter than that of the female thread of the abutment; and (b) a stepped screw member comprising a small-diameter screw portion threadably engageable with the female thread of the abutment, and a large-diameter screw portion threadably engageable with the female thread of the keeper body; the keeper body being strongly fixed to the abutment by the stepped screw member, when the keeper body is rotated in a threadably engaging direction, after the female thread of the abutment threadably engages the small-diameter screw portion, and after the female thread of the keeper body threadably engages the large-diameter screw portion.

The method of the present invention for fixing the keeper for an implant to an abutment comprises the steps of threadably engaging the female thread of the abutment with the small-diameter screw portion of the stepped screw member, threadably engaging the female thread of the keeper body with the large-diameter screw portion of the stepped screw member, and then rotating the keeper body in a threadably engaging direction to strongly fix the keeper body to the abutment by the stepped screw member.

It is preferable that the stepped screw member comprises a step portion or a tapered portion between the small-diameter screw portion and the large-diameter screw portion; and that when the stepped screw member threadably engages the female thread of the abutment until the step portion or tapered portion engages an upper end surface of the abutment, the stepped screw member can be precisely positioned in an axial direction.

The keeper assembly of the present invention for an implant, which is fixed to an implant body implanted in the jawbone, comprises (a) an abutment comprising a head, a female thread extending along a center axis of the head, and a male screw portion projecting downward from the head and threadably engageable with the implant body; (b) a keeper body made of a soft-magnetic material, which comprises a recess for receiving the head of the abutment, and a female thread extending along a center axis to have communication with the recess and having a larger nominal diameter than that of the female thread of the abutment; and (c) a stepped screw member comprising a small-diameter screw portion threadably engageable with the female thread of the abutment, and a large-diameter screw portion threadably engageable with the female thread of the keeper body; the keeper body being strongly fixed to the abutment by the stepped screw member when the keeper body is rotated in a threadably engaging direction after the female thread of the abutment threadably engages the small-diameter screw portion of the stepped screw member, and after the female thread of the keeper body threadably engages the large-diameter screw portion of the stepped screw member.

In the above keeper for an implant and its assembly, it is preferable that the stepped screw member comprises a step portion or a tapered portion between the small-diameter screw portion and the large-diameter screw portion; and that when the stepped screw member threadably engages the female thread of the abutment until the step portion or tapered portion engages an upper end surface of the abutment, the stepped screw member can be precisely positioned in an axial direction.

It is preferable that at least part of the head of the abutment is frustoconical, and that an inner surface of the recess of the keeper body is conical complementarily to the frustoconical portion of the abutment head, so that when the keeper body is fixed to the abutment, the frustoconical portion of the abutment head is brought into close contact with the inner surface of the recess of the keeper body.

At least part of a side surface of the keeper body preferably has a nut shape, so that the keeper body can be rotated in a threadably engaging direction using a tool engageable with the nut-shaped side surface.

The abutment preferably comprises a flange radially projecting outward from a lower end of the head, the flange having a peripheral upper surface portion abutting a peripheral portion of the keeper body, and a lower surface abutting an upper end surface of the implant body.

It is preferable that the head of the abutment is inclined from a center axis of the implant body; that the abutment comprises a hollow cylindrical portion, which is to be inserted into a center hole of the implant body, and a through-hole extending from the hollow cylindrical portion to a side surface of the head; and that the abutment is fixed to the implant body by threadably engaging a screw member penetrating the through-hole and the hollow cylindrical portion with the female thread of the implant body.

BRIEF DESCRIPTION OF THE DRAWINGS

FIG. 11($b$) is a partial cross-sectional view showing the stepped screw member of FIG. 11($a$).

FIG. 12($b$) is a partial cross-sectional view showing a stepped screw member threadably engaging an abutment.

FIG. 12($c$) is a partial cross-sectional view showing a keeper body attached to the stepped screw member threadably engaging the abutment.

FIG. 12($d$) is a partial cross-sectional view showing a keeper body in the course of threadably engaging the stepped screw member threadably engaging the abutment.

FIG. 12($e$) is a partial cross-sectional view showing a keeper body rotated in a threadably engaging direction after the stepped screw member threadably engages the abutment and the keeper body.

FIG. 12($f$) is a partial cross-sectional view showing a keeper body strongly fastened to the abutment with the stepped screw member.

DESCRIPTION OF THE PREFERRED EMBODIMENTS

The embodiments of the present invention will be explained in detail below referring to the attached drawings. Explanations on one embodiment are applicable to other embodiments unless otherwise mentioned. Also, the depicted examples are not restrictive, but may be subject to various modifications within the scope of the present invention.

[1] First Embodiment (a) Structure

Figure 1:
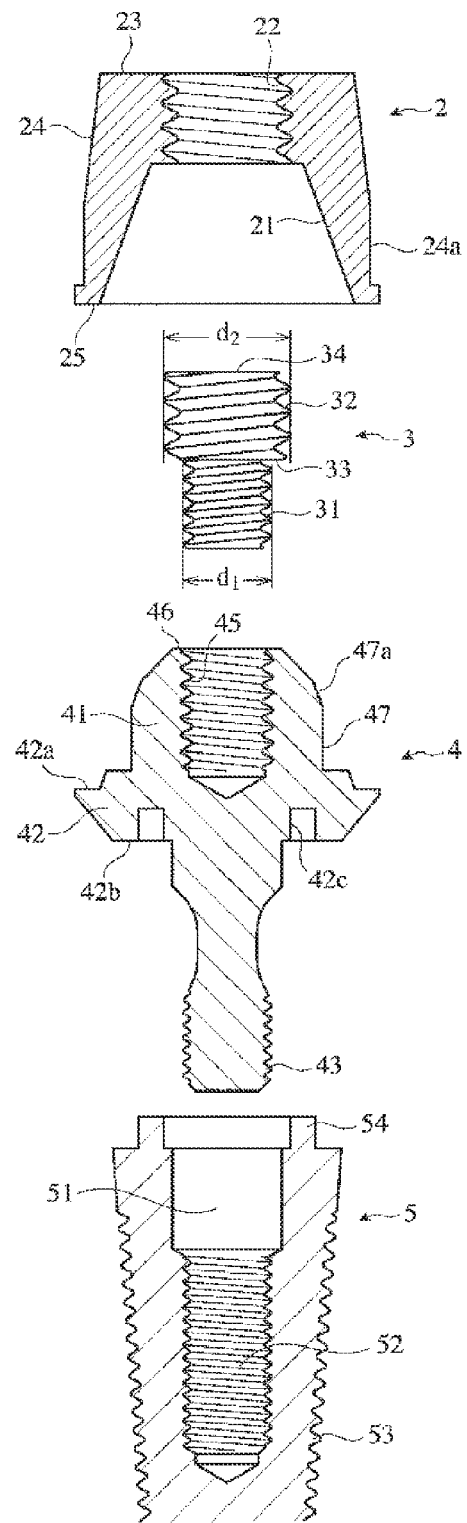
FIG. 1 is an exploded cross-sectional view showing a keeper assembly for an implant according to the first embodiment of the present invention.
Figure 2:
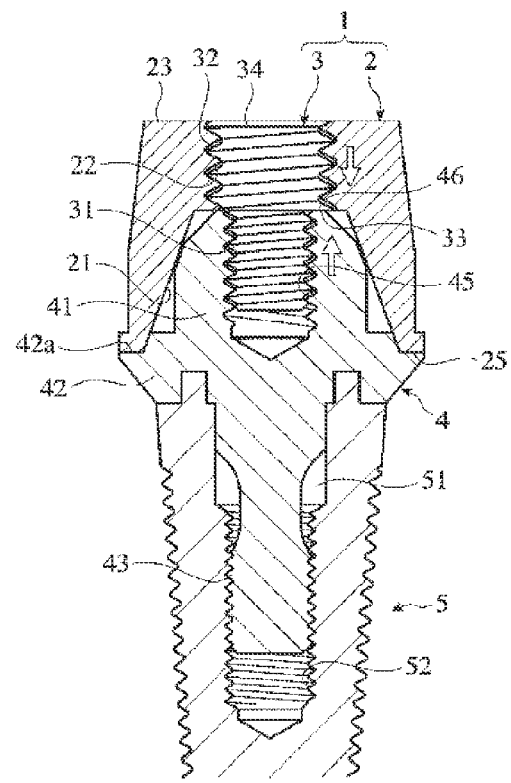
FIG. 2 is a partial cross-sectional view showing the keeper assembly for an implant of FIG. 1.
Figure 3:
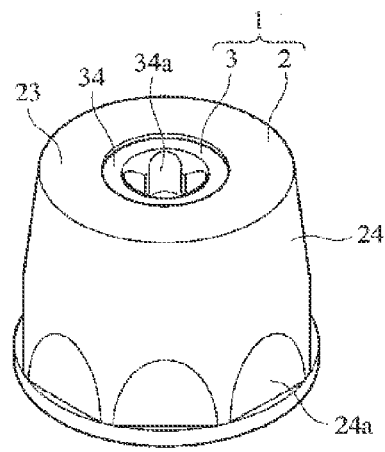
FIG. 3 is a perspective view showing a keeper for an implant according to the first embodiment of the present invention.
Figure 4:
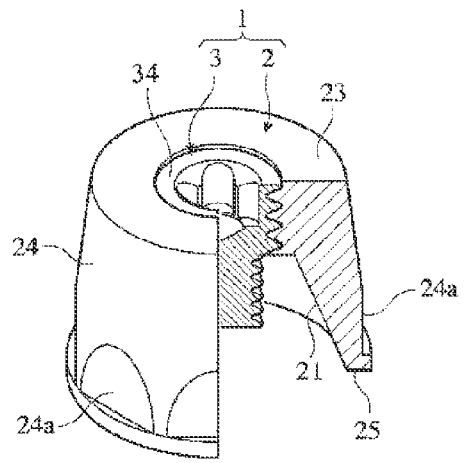
FIG. 4 is a partially cross-sectional perspective view showing the keeper for an implant of FIG. 3.
Figure 5:
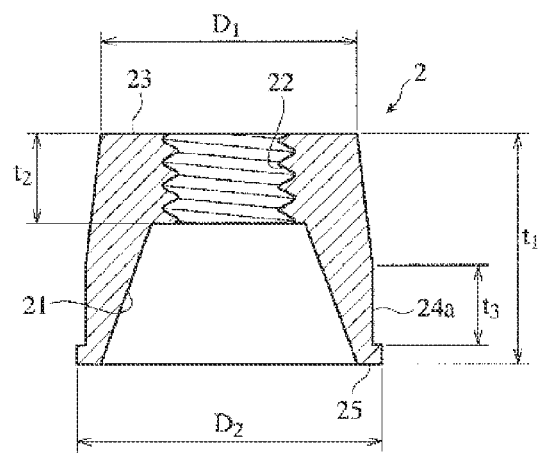
FIG. 5 is a cross-sectional view showing a keeper body used in the first embodiment of the present invention.

A keeper for an implant and its assembly according to the first embodiment of the present invention are shown in FIGS. 1 and 2. The keeper assembly for an implant, which is to be fixed to an implant body 5, comprises an abutment 4 threadably engageable with the implant body 5, and a keeper 1 which comprises a keeper body 2 having a threaded hole 22, and a stepped screw member 3 threadably engageable with the threaded hole 22 of the keeper body 2 and a threaded hole 45 of a head 41 of the abutment 4.

The implant body 5 is a cylindrical member having a male screw portion 53 on a side surface to be implanted in the jawbone, a center hole 51 for receiving a lower male screw 43 of the abutment 4, a female thread 52 formed on the deeper side of the center hole 51 for threadably engaging the male screw 43, and a circular ridge 54 projecting from an upper end surface concentrically with the center hole 51. The implant body 5 preferably has an outer diameter of about 3-6.5 mm and a length of about 10 mm suitable for a usual implant treatment. From the aspect of biocompatibility with the jawbone, corrosion resistance and mechanical strength, the implant body 5 is preferably made of pure titanium or a titanium alloy. To improve the biocompatibility, it may be coated with hydroxyapatite.

The abutment 4 comprises a head 41 engageable with a tapered recess 21 of the keeper 1, a flange 42 radially projecting outward from a lower end of the head 41, and a lower male screw 43 threadably engageable with the female thread 52 of the implant body 5. The flange 42 has a stepped upper surface, whose outer, lower-height, upper surface portion 42a abuts a bottom edge 25 of the keeper body 2. A lower surface 42b of the flange 42, which is brought into contact with an upper end surface of the implant body 5, comprises a circular recess 42c engageable with the circular ridge 54 of the implant body 5. The head 41 of the abutment 4 comprises a female thread 45 open at a center of the upper end surface, and a nut-shaped side surface 47, part of which is a tapered surface 47a engageable with the tapered recess 21 of the keeper 1. The abutment 4 is preferably made of the same material as that of the implant body 5.

As shown in FIGS. 1-6, the frustoconical keeper body 2 comprises a tapered recess 21 for receiving the head 41 of the abutment 4, and a female thread 22 open at a center of the upper surface 23 for communication with the tapered recess 21. The female thread 22 of the keeper body 2 has a larger nominal diameter than that of the female thread 45 of the abutment 4. The keeper body 2 having a height t1 is frustoconical (D1<D2), part of its conical side surface 24 constituting, for example, an octagonal nut 24a having a height t3, about ½ of t1. Of course, the octagonal nut is an example, and a hexagonal nut whose opposing surfaces have a distance meeting the requirement of JIS B 1181 may be acceptable. The size of the upper surface 23 of the keeper body 2 is properly determined depending on the size of a magnetic denture attachment 9 (see FIG. 7). Because the tapered recess 21 of the keeper body 2 is complementary to the tapered surface 47a of the head 41 of the abutment 4, the tapered recess 21 strongly engages the tapered surface 47a.

The stepped screw member 3 comprises a small-diameter screw portion 31 threadably engageable with the female thread 45 of the abutment 4, and a large-diameter screw portion 32 coaxially and integrally connected to the small-diameter screw portion 31 and threadably engageable with the female thread 22 of the keeper body 2, with a step portion 33 between the small-diameter screw portion 31 and the large-diameter screw portion 32. When the stepped screw member 3 threadably engages the female thread 45 of the abutment 4, the step portion 33 of the stepped screw member 3 engages the upper end surface 46 of the abutment 4, acting as a stopper for positioning the stepped screw member 3 precisely in an axial direction. The stepped screw member 3 has a driver-engaging, clover-shaped recess 34a on a flat upper end surface 34. In place of the clover-shaped recess 34a, a slot according to JIS B 1117 or a hexagonal recess according to JIS B 1177 may be used.

In the stepped screw member 3, the small-diameter screw portion 31 preferably has a nominal diameter d1 of about 1.2-1.8 mm, and the large-diameter screw portion 32 preferably has a nominal diameter d2 of about 1.6-3.0 mm. To act as a screw, the small-diameter screw portion 31 should have a nominal diameter d1 of at least about 1.2 mm. Also, when the nominal diameter d2 of the large-diameter screw portion 32 is more than 3.0 mm, the upper surface 23 of the keeper body 2 has a small area, resulting in small attraction to the magnetic denture attachment. The step portion 33 of the stepped screw member 3 should be large enough to stop the upper end surface of the abutment 4, when the stepped screw member 3 threadably engages the abutment 4. To this end, a ratio d2/d1 of the nominal diameter d2 of the large-diameter screw portion 32 to the nominal diameter d1 of the small-diameter screw portion 31 is preferably about 1.2-1.5.

The keeper body 2 should be made of a soft-magnetic material, preferably ferritic stainless steel (see JIS G 4303) having excellent soft-magnetic properties and corrosion resistance, to be magnetically attached to the magnetic denture attachment. Like the keeper body 2, the stepped screw member 3 is also preferably made of a soft-magnetic material to be magnetically attached to the magnetic denture attachment, though it may be made of a non-magnetic material such as titanium because it is a small member.

(b) Fixing Method

To fix the above keeper 1 for an implant to the abutment 4, the male screw 43 of the abutment 4 is threadably engaged with the female thread 52 of the implant body 5 implanted in the jawbone, to fix the abutment 4 to the implant body 5. Using a driver fit in the clover-shaped recess 34a, the small-diameter screw portion 31 of the stepped screw member 3 is threadably engaged with the female thread 45 of the abutment 4, until the step portion 33 of the stepped screw member 3 abuts the upper end surface 46 of the abutment 4. The female thread 22 of the keeper body 2 placed on the abutment 4 is then threadably engaged with the large-diameter screw portion 32 of the stepped screw member 3. The keeper body 2 is rotated in a threadably engaging direction, until the bottom edge 25 of the keeper body 2 abuts the peripheral upper surface portion 42a of the flange 42 of the abutment 4, or until the tapered recess 21 of the keeper body 2 abuts the upper end surface 46 of the head 41 of the abutment 4.

The keeper body 2 in contact with the abutment 4 is rotated by a wrench in a threadably engaging direction (usually in a right-hand thread direction) to be strongly fixed to the abutment 4. In this case, the upper end surface 34 of the stepped screw member 3 should be avoided from projecting from the upper surface 23 of the keeper body 2. Namely, the upper end surface 34 of the stepped screw member 3 should be substantially in alignment with or slightly lower than the upper surface 23 of the keeper body 2. Because threadable engagement causes the step portion 33 of the stepped screw member 3 to abut the upper end surface 46 of the abutment 4, the upper end surface 34 of the stepped screw member 3 can be positioned precisely and easily by making the length of the large-diameter screw portion 32 of the stepped screw member 3 equal to or slightly less than that of the female thread 22 of the keeper body 2. Also, the engagement of the step portion 33 of the stepped screw member 3 with the upper end surface 46 of the abutment 4 sets the threadably engaging position of the keeper body 2 with the stepped screw member 3.

Figure 6:
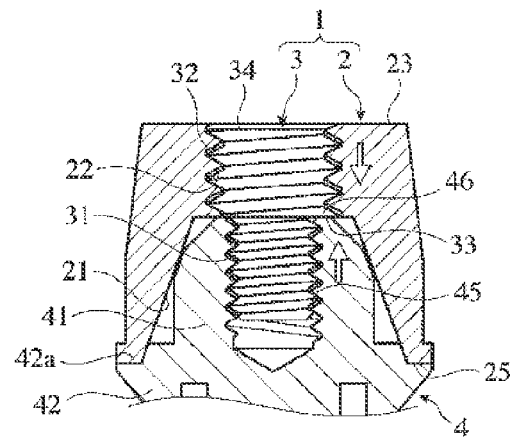
FIG. 6 is a partial cross-sectional view showing the keeper for an implant of FIG. 3 threadably engaging an abutment.

As shown in FIGS. 2 and 6, with the keeper body 2 threadably engaging the stepped screw member 3, lower sides of screw ridges in the large-diameter screw portion 32 of the stepped screw member 3 push upper sides of screw ridges in the female thread 22 of the keeper body 2, while upper sides of screw ridges in the small-diameter screw portion 31 of the stepped screw member 3 push lower sides of screw ridges in the female thread 45 of the abutment 4. Namely, the stepped screw member 3 pushes the keeper body 2 downward and the abutment 4 upward. Accordingly, the keeper body 2 is strongly fixed to the abutment 4 without loosening even under a repeated load.

(c) Magnetic Attachment

Figure 7:
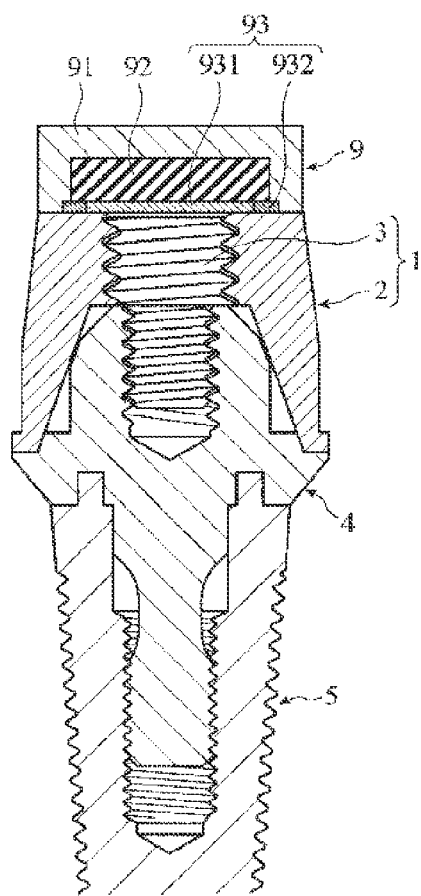
FIG. 7 is a partial cross-sectional view showing a magnetic attachment attracted to the keeper assembly for an implant of FIG. 1.

As shown in FIG. 7, a magnetic attachment 9 of a denture is magnetically attached to the upper surface 23 of the keeper body 2 to fix the denture. The magnetic attachment 9 per se may be a known one (see, for example, WO 2005/077297). The magnetic attachment 9 shown in FIG. 7 comprises a soft-magnetic, cup-shaped yoke 91 having a circular-cross-sectioned recess, a disc-shaped permanent magnet 92 magnetized in a thickness direction and received in the circular-cross-sectioned recess, and a seal plate 93 for sealing the recess. The seal plate 93, a member sealing the permanent magnet 92 in the circular-cross-sectioned recess and acting as a magnetic path, is constituted by a disc-shaped yoke 931 of a soft-magnetic material, and a seal ring 932 of a non-magnetic material attached to a periphery of the yoke 931. The above soft-magnetic material is preferably a corrosion-resistant metal such as ferritic stainless steel (for example, SUS447J1), and the above non-magnetic material is preferably a corrosion-resistant metal such as austenitic stainless steel (for example, SUS316L).

The permanent magnet 92 is suitably formed by a sintered R-T-B magnet (for example, anisotropic sintered Nd—Fe—B magnet) having high magnetic properties. This sintered magnet preferably has a composition comprising 27-34% by mass of R, which is at least one of rare earth elements including Y, at least one of Nd, Dy and Pr being indispensable, and 0.6-1.8% by mass of B, the balance being substantially T (Fe or Co). Less than 27% by mass of R provides too low coercivity (iHc), and more than 34% by mass of R provides an extremely decreased residual magnetic flux density Br. Less than 0.6% by mass of B fails to provide practically acceptable coercivity, and more than 1.8% by mass of B provides extremely decreased Br. The more preferred composition of the sintered R-T-B magnet comprises 27-32% by mass of R, 0.6-1.8% by mass of B, 0.0001-20% by mass of Co, and 0.001-3% by mass of M, which is at least one selected from the group consisting of Al, Si, Cu, Ga, Nb, Mo and W, the balance being substantially Fe.

[2] Second Embodiment (a) Structure

Figure 8:
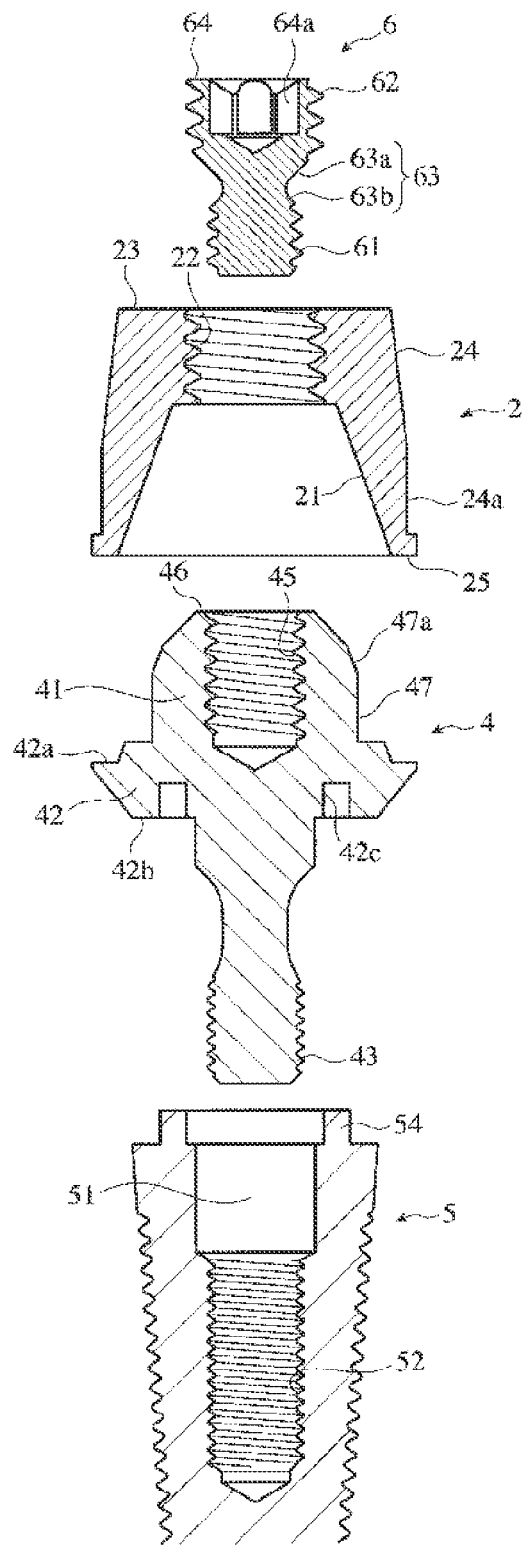
FIG. 8 is an exploded cross-sectional view showing a keeper assembly for an implant according to the second embodiment of the present invention.
Figure 9:
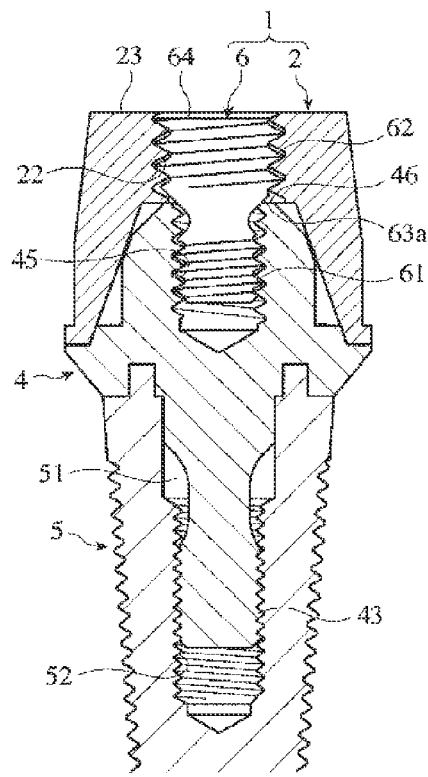
FIG. 9 is a partial cross-sectional view showing the keeper assembly for an implant of FIG. 8.
Figure 10:
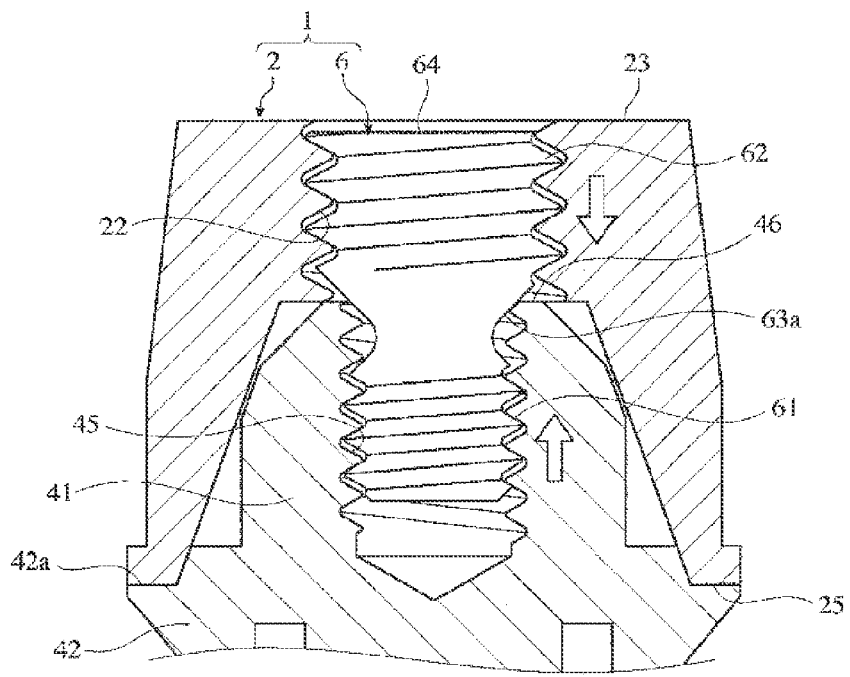
FIG. 10 is an enlarged, partial cross-sectional view showing the keeper for an implant according to the second embodiment of the present invention fixed to an abutment.
Figure 11A:
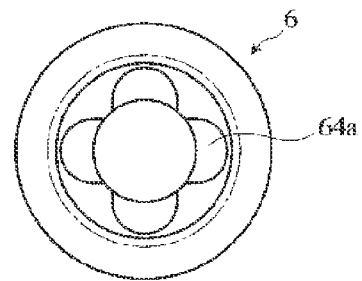
FIG. 11($a$) is a plan view showing a stepped screw member used in the second embodiment of the present invention.
Figure 11B:
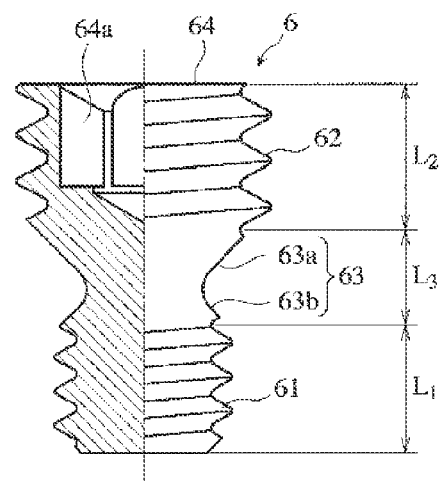

A keeper for an implant and its assembly according to the second embodiment of the present invention are shown in FIGS. 8-10. The second embodiment is basically the same as the first embodiment, except for using a stepped screw member 6 shown in FIG. 11 as a screw member for the keeper body 2.

The stepped screw member 6 integrally comprises a small-diameter screw portion 61 (length: $L_1$) threadably engageable with the female thread 45 of the abutment 4, a small-diameter, thread-free portion 63 (length: $L_3$), and a large-diameter screw portion 62 (length: $L_2$) threadably engageable with the female thread 22 of the keeper body 2 in this order from below along a center axis. The small-diameter portion 63 comprises a first tapered portion 63a having a diameter decreasing from the large-diameter screw portion 62 toward the small-diameter screw portion 61, and a second tapered portion 63b having a diameter decreasing from the small-diameter screw portion 61 toward the large-diameter screw portion 62. The upper end surface 64 of the stepped screw member 6 is provided with a clover-shaped recess 64a, in which a driver is fit. In place of the clover-shaped recess 64a, a slot according to JIS B 1117 or a hexagonal recess according to JIS B 1177 may be used. The small-diameter screw portion 61 and large-diameter screw portion 62 of the stepped screw member 6 may have the same nominal diameters as those of the stepped screw member 3.

(b) Fixing Method

Figure 12A:
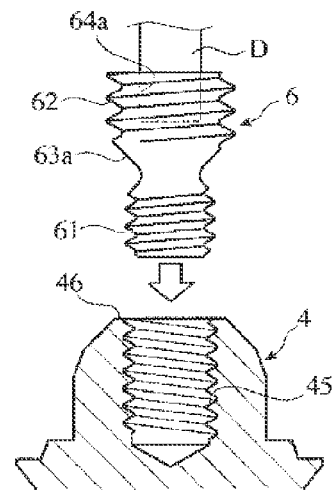
FIG. 12($a$) is a partial cross-sectional view showing a stepped screw member immediately before threadably engaging an abutment, to cause the keeper for an implant according to the second embodiment of the present invention to threadably engage the abutment.
Figure 12B:
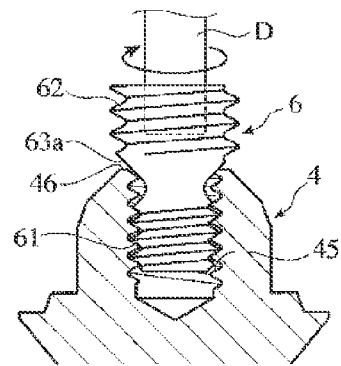
Figure 12C:
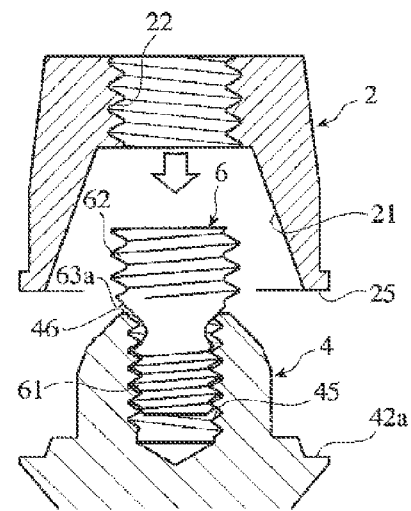

To fix the above keeper 1 to the abutment 4, the small-diameter screw portion 61 of the stepped screw member 6 is threadably engaged with the female thread 45 of the abutment 4 by a tool D fit in the clover-shaped recess 64a as shown in FIG. 12(a), and the stepped screw member 6 is then rotated in a threadably engaging direction, until the first tapered portion 63a of the stepped screw member 6 abuts the upper end surface 46 of the abutment 4 as shown in FIG. 12(b). As a result, the stepped screw member 6 is fixed to the abutment 4, with upper sides of screw ridges in the small-diameter screw portion 61 of the stepped screw member 6 pushing lower sides of screw ridges in the female thread 45 of the abutment 4 as shown in FIG. 12(c). With the female thread 22 of the keeper body 2 and the large-diameter screw portion 62 of the stepped screw member 6 having proper lengths determined in advance, the abutment of the first tapered portion 63a of the stepped screw member 6 to the upper end surface 46 of the abutment 4 makes it possible to achieve precise positioning of the upper end surface 64 of the stepped screw member 6 easily. Because the stepped screw member 6 is stopped by the abutment 4 by abutting the first tapered portion 63a of the stepped screw member 6 to the upper end surface 46 of the abutment 4, the threadably engaging position of the stepped screw member 6 does not change in the threadable engagement of the keeper body 2. Accordingly, the first tapered portion 63a may be called "stopper."

Figure 12D:
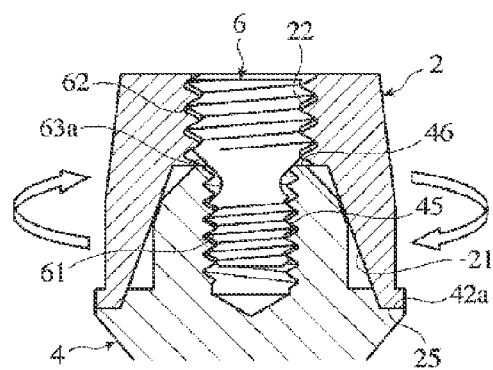
Figure 12E:
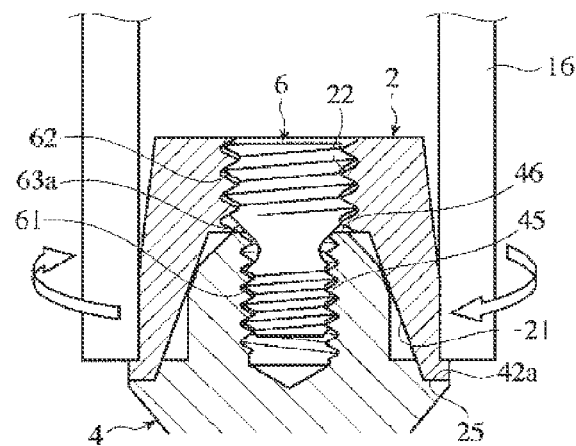

As shown in FIG. 12(d), the female thread 22 of the keeper body 2 placed on the abutment 4 is threadably engaged with the large-diameter screw portion 62 of the stepped screw member 6. The keeper body 2 is then rotated in a threadably engaging direction, until the bottom edge 25 of the keeper body 2 abuts the flange 42 of the abutment 4, or until the tapered recess 21 of the keeper body 2 abuts the upper end surface 46 of the head 41 of the abutment 4. As shown in FIG. 12(e), the keeper body 2 is rotated in a threadably engaging direction by a wrench 16 with a predetermined torque (for example, 20-30 N·cm), so that the stepped screw member 6 strongly fixes the keeper body 2 to the abutment 4. Because the female thread 22 of the keeper body 2 and the large-diameter screw portion 62 of the stepped screw member 6 have properly predetermined lengths as described above, the upper end surface 64 of the stepped screw member 6 does not project from the upper surface 23 of the keeper body 2 (substantially in alignment with or slightly lower than the upper surface 23 of the keeper body 2).

Figure 12F:
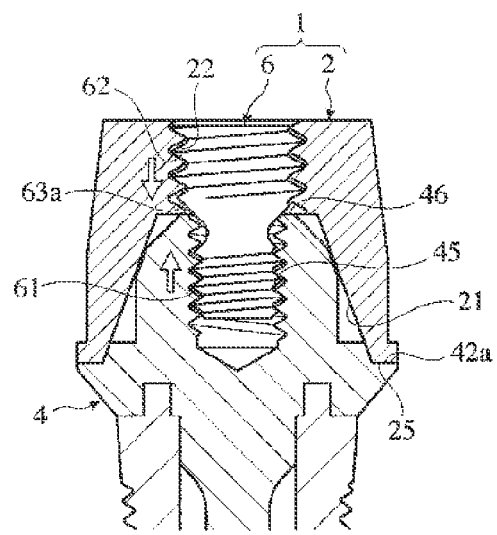

As shown in FIGS. 10 and 12(f), the threadable engagement of the keeper body 2 makes lower sides of screw ridges in the large-diameter screw portion 62 of the stepped screw member 6 push upper sides of screw ridges in the female thread 22 of the keeper body 2, and upper sides of screw ridges in the small-diameter screw portion 61 of the stepped screw member 6 push lower sides of screw ridges in the female thread 45 of the abutment 4. Namely, the stepped screw member 6 pushes the keeper body 2 downward and the abutment 4 upward. Accordingly, the keeper body 2 is strongly fixed to the abutment 4 without loosening even under a repeated load.

Instead of the procedure shown in FIGS. 12(a)-12(d), after the large-diameter screw portion 62 of the stepped screw member 6 threadably engages the female thread 22 of the keeper body 2, the female thread 45 of the abutment 4 may threadably engage the small-diameter screw portion 61 of the stepped screw member 6. In this case, when the stepped screw member 6 is threadably engaged with the female thread 45 of the abutment 4 until the first tapered portion 63a of the stepped screw member 6 abuts the upper end surface 46 of the abutment 4, the stepped screw member 6 engages the abutment 4 with upper sides of screw ridges in the small-diameter screw portion 61 of the stepped screw member 6 pushing lower sides of screw ridges in the female thread 45 of the abutment 4. Also, after the keeper body 2 is placed on the abutment 4, the stepped screw member 6 may threadably engage the female thread 22 of the keeper body 2 and the female thread 45 of the abutment 4 successively.

[3] Third Embodiment

Figure 13:
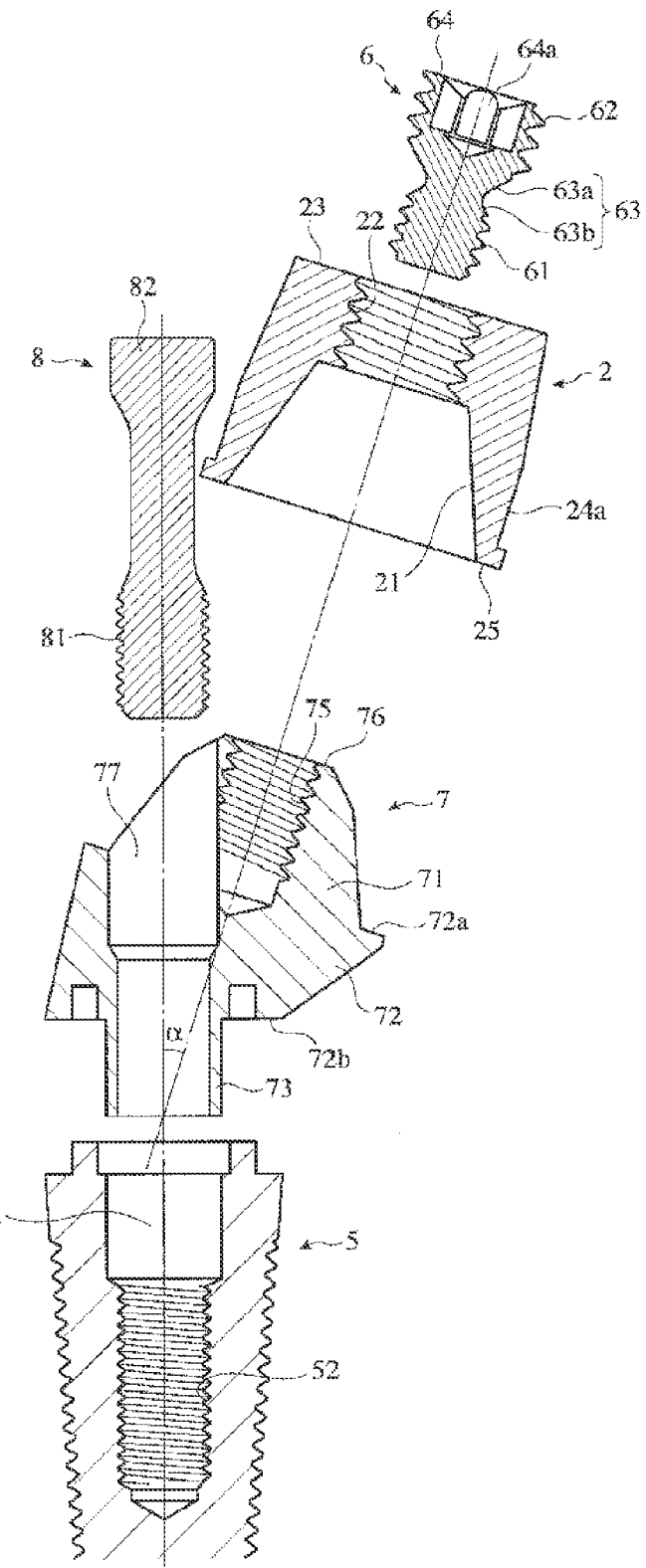
FIG. 13 is an exploded cross-sectional view showing a keeper assembly for an implant according to the third embodiment of the present invention.
Figure 14:
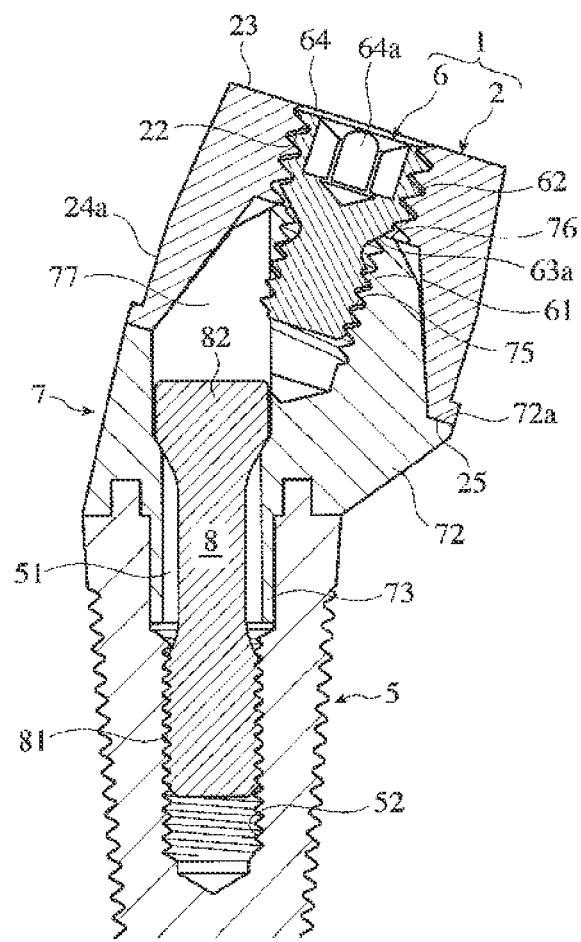
FIG. 14 is a partial cross-sectional view showing the keeper assembly for an implant of FIG. 13.
Figure 15:
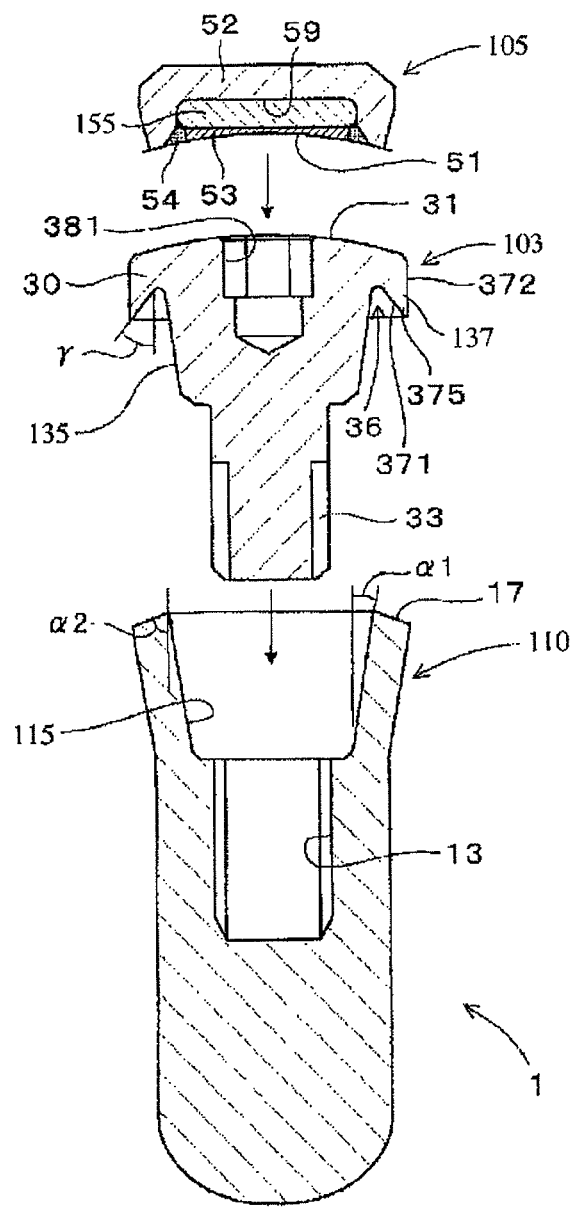
FIG. 15 is an exploded cross-sectional view showing the magnetic dental attachment described in U.S. Pat. No. 6,709,270.
Figure 16:
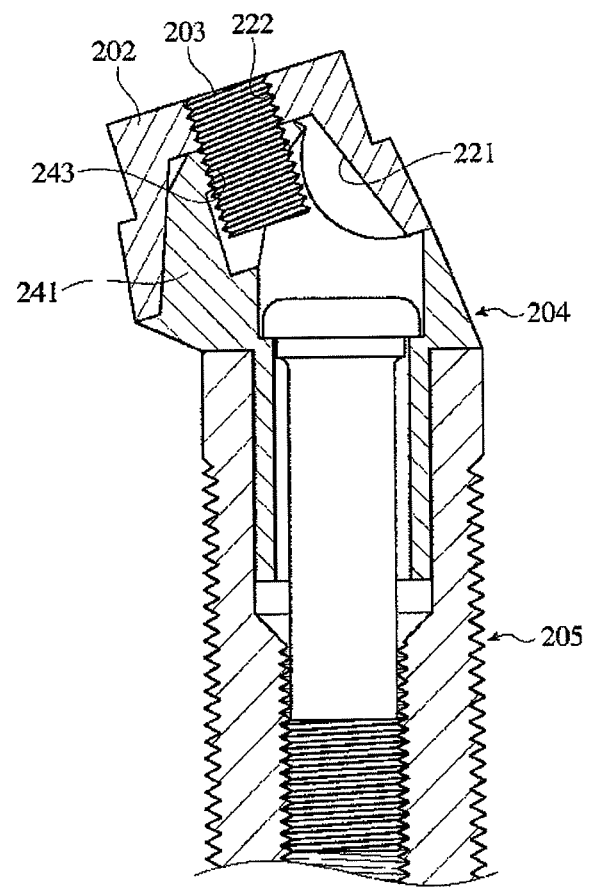
FIG. 16 is a cross-sectional view showing the keeper assembly for an implant described in JP 2009-131620 A.

A keeper for an implant and its assembly according to the third embodiment of the present invention are shown in FIGS. 13 and 14. This keeper assembly for an implant comprises an abutment 7 threadably engageable with the implant body 5 by a screw 8, and a keeper 1 fixed to a head 71 of the abutment 7. The keeper 1 comprises a keeper body 2 and a stepped screw member 6. The keeper 1 and the implant body 5 may be the same as in the second embodiment.

The abutment 7 comprises a head 71 engageable with the keeper body 2, a large-diameter portion 72 connected to a lower end of the head 71, and a hollow cylindrical portion 73 coaxially communicating with a through-hole 77 extending in the head 71 and projecting from a lower surface 72b of the large-diameter portion 72. A peripheral upper surface portion 72a of the large-diameter portion 72 abuts a bottom edge 25 of the keeper 1. The head 71 of the abutment 7 has a female thread 75 open on an upper end surface 76, and the female thread 75 threadably engages the small-diameter screw portion 61 of the stepped screw member 6. Because the first tapered portion 63a of the stepped screw member 6 threadably engageable with the female thread 75 abuts the upper end surface 76 of the head 71, an upper end surface of the large-diameter screw portion 62 of the stepped screw member 6 appearing in the head 71 of the abutment 7 is substantially in alignment with or slightly lower than the upper surface 23 of the keeper body 2.

Because the head 71 of the abutment 7 and its female thread 75 are inclined from the hollow cylindrical portion 73 (through-hole 77) by an angle α, the through-hole 77, into which the screw 8 is inserted, is open on a side surface of the head 71. The angle α is preferably in a range of 15-35°, more preferably 15-30°.

After the hollow cylindrical portion 73 of the abutment 7 is inserted into the center hole 51 of the implant body 5, the screw member 8 is inserted into the through-hole 77 of the abutment 7, and the male screw 81 of the screw member 8 is threadably engaged with the female thread 52 of the implant body 5 to fix the abutment 7 to the implant body 5. The method for threadably engaging the keeper 1 to the abutment 7 may be the same as in the second embodiment.

EFFECT OF THE INVENTION

Because the stepped screw member having a large-diameter screw portion and a small-diameter screw portion is used in the present invention, tensions in opposite directions are applied to the large-diameter screw portion threadably engaging the female thread of the keeper body made of a soft-magnetic material, and the small-diameter screw portion threadably engaging the female thread of the abutment, so that the keeper body is strongly fixed to the abutment by the stepped screw member without loosening even after a long period of use. Also, because the stepped screw member has a step portion or a tapered portion between the small-diameter screw portion and the large-diameter screw portion, the step portion or the tapered portion engages the upper end surface of the abutment, when the stepped screw member threadably engages the female thread of the abutment, easily achieving the precise positioning of the stepped screw member in an axial direction (preventing the deviation of the threadably engaging position).

Because the keeper for an implant of the present invention has a small number of parts, and is easily fixed to the abutment, it makes it possible to operate a dental implant treatment in a short period of time.

What is claimed is:

1. A keeper for an implant comprising
   (a) a keeper body made of a soft-magnetic material, which comprises a recess for receiving a head of an abutment having a female thread, and a female thread extending along a center axis to have communication with said recess and having a larger nominal diameter than that of the female thread of said abutment; and
   (b) a stepped screw member comprising a small-diameter screw portion threadably engageable with the female thread of said abutment, and a large-diameter screw portion threadably engageable with the female thread of said keeper body;
   said keeper body being strongly fixed to said abutment by said stepped screw member, when said keeper body is rotated in a threadably engaging direction, after the female thread of said abutment threadably engages said small-diameter screw portion, and after the female thread of said keeper body threadably engages said large-diameter screw portion.

2. The keeper for an implant according to claim 1, wherein said stepped screw member comprises a step portion or a tapered portion between said small-diameter screw portion and said large-diameter screw portion; and wherein when said stepped screw member threadably engages said female thread of said abutment until said step portion or tapered portion engages an upper end surface of said abutment, said stepped screw member can be precisely positioned in an axial direction.

3. The keeper for an implant according to claim 1, wherein at least part of the head of said abutment is frustoconical, and an inner surface of the recess of said keeper body is conical complementarily to the frustoconical portion of said abutment head, so that when said keeper body is fixed to said abutment, said frustoconical portion of said abutment head is brought into close contact with the inner surface of said recess of said keeper body.

4. The keeper for an implant according to claim 1, wherein at least part of a side surface of said keeper body has a nut shape, so that said keeper body can be rotated in a threadably engaging direction using a tool engageable with said nut-shaped side surface.

5. A method for fixing the keeper for an implant recited in claim 1 to an abutment, comprising the steps of threadably engaging the female thread of said abutment with the small-diameter screw portion of said stepped screw member, threadably engaging the female thread of said keeper body with the large-diameter screw portion of said stepped screw member, and then rotating said keeper body in a threadably engaging direction to strongly fix said keeper body to said abutment by said stepped screw member.

6. A method for fixing the keeper for an implant recited in claim 5 to an abutment, said stepped screw member comprising a step portion or a tapered portion between said small-diameter screw portion and said large-diameter screw portion, the method comprising the steps of threadably engaging the small-diameter screw portion of said stepped screw member with the female thread of said abutment, until said step portion or tapered portion abuts an upper end surface of said abutment; threadably engaging the large-diameter screw portion of said stepped screw member with the female thread of said keeper body, and then rotating said keeper body in a threadably engaging direction.

7. A keeper assembly for an implant, which is fixed to an implant body implanted in the jawbone, comprising
    (a) an abutment comprising a head, a female thread extending along a center axis of said head, and a male screw portion projecting downward from said head and threadably engageable with said implant body;
    (b) a keeper body made of a soft-magnetic material, which comprises a recess for receiving the head of said abutment, and a female thread extending along a center axis to have communication with said recess and having a larger nominal diameter than that of the female thread of said abutment; and
    (c) a stepped screw member comprising a small-diameter screw portion threadably engageable with the female thread of said abutment, and a large-diameter screw portion threadably engageable with the female thread of said keeper body, with a step-shaped stopper between said small-diameter screw portion and said large-diameter screw portion;
    said keeper body being strongly fixed to said abutment by said stepped screw member when said keeper body is rotated in a threadably engaging direction after the female thread of said abutment threadably engages the small-diameter screw portion of said stepped screw member, and after the female thread of said keeper body threadably engages the large-diameter screw portion of said stepped screw member.

8. The keeper assembly for an implant according to claim 7, wherein said stepped screw member comprises a step portion or a tapered portion between said small-diameter screw portion and said large-diameter screw portion; and wherein said stepped screw member can be precisely positioned in an axial direction, when said stepped screw member threadably engages said female thread of said abutment until said step portion or tapered portion engages an upper end surface of said abutment.

9. The keeper assembly for an implant according to claim 7, wherein at least part of the head of said abutment is frustoconical, and an inner surface of the recess of said keeper body is conical complementarily to the frustoconical portion of said abutment head, so that when said keeper body is fixed to said abutment, said frustoconical portion of said abutment head is brought into close contact with the inner surface of said recess of said keeper body.

10. The keeper assembly for an implant according to claim 7, wherein at least part of a side surface of said keeper body has a nut shape, and wherein said keeper body is rotated in a threadably engaging direction using a tool engageable with said nut-shaped side surface.

11. The keeper assembly for an implant according to claim 7, wherein said abutment comprises a flange radially projecting outward from a lower end of said head, said flange having a peripheral upper surface portion abutting a peripheral portion of said keeper body, and a lower surface abutting an upper end surface of said implant body.

12. A keeper assembly for an implant, which is fixed to an implant body implanted in the jawbone, comprising
    (a) an abutment comprising a head inclined from a center axis of said implant body, a female thread extending along a center axis of said head, a hollow cylindrical portion extending along a center axis of said implant body which is to be inserted into a center hole of said implant body and a through-hole extending from said hollow cylindrical portion to a side surface of said head;
    (b) a screw member having a male screw which is passed through said through-hole and said hollow cylindrical portion of said abutment to be threadably engaged with a female thread of said implant body;
    (c) a keeper body made of a soft-magnetic material, which comprises a recess for receiving the head of said abutment, and a female thread extending along a center axis to have communication with said recess and having a larger nominal diameter than that of the female thread of said abutment; and
    (d) a stepped screw member comprising a small-diameter screw portion threadably engageable with the female thread of said abutment, and a large-diameter screw portion threadably engageable with the female thread of said keeper body, with a step-shaped stopper between said small-diameter screw portion and said large-diameter screw portion;
    said keeper body being strongly fixed to said abutment by said stepped screw member when said keeper body is rotated in a threadably engaging direction after the female thread of said abutment threadably engages the small-diameter screw portion of said stepped screw member, and after the female thread of said keeper body threadably engages the large-diameter screw portion of said stepped screw member; and
    said abutment being fixed to said implant body by threadably engaging said male screw of said screw member with said female thread of said implant body.

13. The keeper assembly for an implant according to claim 12, wherein said stepped screw member comprises a step portion or a tapered portion between said small-diameter screw portion and said large-diameter screw portion; and wherein said stepped screw member can be precisely positioned in an axial direction, when said stepped screw member threadably engages said female thread of said abutment until said step portion or tapered portion engages an upper end surface of said abutment.

14. The keeper assembly for an implant according to claim 12, wherein at least part of the head of said abutment is frustoconical, and an inner surface of the recess of said keeper body is conical complementarily to the frustoconical portion of said abutment head, so that when said keeper body is fixed to said abutment, said frustoconical portion of said abutment head is brought into close contact with the inner surface of said recess of said keeper body.

15. The keeper assembly for an implant according to claim 12, wherein at least part of a side surface of said keeper body has a nut shape, and wherein said keeper body is rotated in a threadably engaging direction using a tool engageable with said nut-shaped side surface.

16. The keeper assembly for an implant according to claim 12, wherein said abutment comprises a large-diameter portion connected to a lower end of said head, said large-diameter portion having a peripheral upper surface portion abutting a bottom edge of said keeper body, and a lower surface abutting an upper end surface of said implant body.

* * * * *